(12) United States Patent
Lafontaine

(10) Patent No.: US 8,142,457 B2
(45) Date of Patent: Mar. 27, 2012

(54) PERCUTANEOUS TRANSLUMINAL ENDARTERECTOMY

(75) Inventor: Daniel M. Lafontaine, Plymouth, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 2745 days.

(21) Appl. No.: 10/397,622

(22) Filed: Mar. 26, 2003

(65) Prior Publication Data
US 2004/0193204 A1    Sep. 30, 2004

(51) Int. Cl.
*A61B 17/22* (2006.01)
*A61B 17/00* (2006.01)
*A61D 1/02* (2006.01)

(52) U.S. Cl. ........................... 606/159; 606/190

(58) Field of Classification Search .......... 606/190, 606/159
See application file for complete search history.

(56) References Cited

U.S. PATENT DOCUMENTS

| | | | |
|---|---|---|---|
| 3,481,338 A * | 12/1969 | Sobel et al. ............ | 606/190 |
| 3,525,339 A * | 8/1970 | Halligan ............... | 606/190 |
| 3,730,185 A | 5/1973 | Cook et al. | |
| 3,776,238 A | 12/1973 | Peyman et al. | |
| 3,805,787 A | 4/1974 | Banko | |
| 4,428,748 A | 1/1984 | Peyman et al. | |
| 4,515,583 A | 5/1985 | Sorich | |
| 4,559,927 A | 12/1985 | Chin | |
| 4,589,412 A | 5/1986 | Kensey | |
| 4,631,052 A | 12/1986 | Kensey | |
| 4,749,376 A | 6/1988 | Kensey et al. | |
| 4,765,332 A | 8/1988 | Fischell et al. | |
| 4,804,364 A | 2/1989 | Dieras et al. | |
| 4,819,635 A | 4/1989 | Shapiro | |
| 4,861,332 A | 8/1989 | Parisi | |
| 4,870,953 A | 10/1989 | DonMicheal et al. | |
| 4,911,170 A | 3/1990 | Thomas, III et al. | |
| 4,920,954 A | 5/1990 | Alliger et al. | |
| 4,924,863 A | 5/1990 | Sterzer | |
| 4,950,238 A | 8/1990 | Sullivan | |
| 4,962,755 A | 10/1990 | King et al. | |
| 4,994,067 A | 2/1991 | Summers | |
| 5,042,984 A | 8/1991 | Kensey | |

(Continued)

OTHER PUBLICATIONS

The Mollring Cutter Remote Endarterectomy; Journal of Endovascular Surgery; 1995; 2:278-287.*

*Primary Examiner* — Gary Jackson
*Assistant Examiner* — Michael Mendoza
(74) *Attorney, Agent, or Firm* — Seager, Tufte & Wickhem LLC

(57) ABSTRACT

Methods and devices for performing intravascular endarterectomy. Methods includes intravascularly advancing a catheter having a carbon dioxide delivering distal end past a plaque-occluded vessel site, passing the distal end between the plaque and vessel wall. Other methods include intravascularly advancing paddles between plaque and vessel walls, including ultrasonic imaging paddles, ultrasonic vibrating paddles, and mechanically vibrating paddles. Some methods include providing intravascular devices having radially expandable jaws or paddles, and advancing those jaws or paddles along vessel walls to separate plaque from vessel walls. Still other methods include providing an anchoring guide catheter adapted to establish a suction grip around the left coronary artery ostium, and to use the anchored guide catheter to support intravascularly introduced endarterectomy devices operating on plaque in the left main coronary artery. One method utilizes retroperfusion of the coronary arteries to allow the anchoring guide catheter to remain in position for longer periods. Scissors-type expanding devices and stents for use after endarterectomy procedures are also provided.

10 Claims, 15 Drawing Sheets

U.S. PATENT DOCUMENTS

| | | |
|---|---|---|
| 5,069,664 A | 12/1991 | Guess et al. |
| 5,087,265 A | 2/1992 | Summers |
| 5,092,873 A | 3/1992 | Simpson et al. |
| 5,163,433 A | 11/1992 | Kagawa et al. |
| 5,226,430 A | 7/1993 | Spears et al. |
| 5,269,291 A | 12/1993 | Carter |
| 5,344,395 A | 9/1994 | Whalen et al. |
| 5,380,273 A | 1/1995 | Dubrul et al. |
| 5,397,301 A | 3/1995 | Pflueger et al. |
| 5,409,454 A | 4/1995 | Fischell et al. |
| 5,474,530 A | 12/1995 | Passafaro et al. |
| 5,474,531 A | 12/1995 | Carter |
| 5,480,379 A | 1/1996 | LaRosa |
| 5,725,494 A | 3/1998 | Brisken |
| 5,728,129 A | 3/1998 | Summers |
| 5,879,499 A * | 3/1999 | Corvi ............................ 156/175 |
| 6,468,297 B1 | 10/2002 | Williams et al. |
| 6,565,583 B1 * | 5/2003 | Deaton et al. ................ 606/159 |
| 2002/0029052 A1 * | 3/2002 | Evans et al. ................... 606/159 |
| 2002/0120257 A1 * | 8/2002 | Newman et al. ................ 606/15 |
| 2002/0198551 A1 * | 12/2002 | Grant et al. ................... 606/159 |

* cited by examiner

PERCUTANEOUS TRANSLUMINAL ENDARTERECTOMY

FIELD OF THE INVENTION

The present invention is related generally to medical devices. More specifically, the present invention includes intravascular devices and catheters for performing endarterectomy.

BACKGROUND OF THE INVENTION

Arteriosclerosis is a common vascular disease in which blood vessels become hardened and blocked or partially blocked by plaque that can substantially reduce blood flow. The accumulation of plaque is often a major factor in the occurrence of myocardial infarction, stroke, and high blood pressure.

To treat arteriosclerosis, minimally invasive techniques have been developed. One minimally invasive technique utilizes percutaneous transluminal coronary angioplasty (PTCA), which can include expanding a balloon under pressure within a coronary artery, and dilating a narrowed area of that artery. While PTCA procedures can significantly dilate narrowed coronary arteries, the treated vessel region may become narrow again in a process known as restenosis. In a substantial percentage of PTCA procedures, the dilated vessel region becomes restenosed.

Another example of a minimally invasive technique is atherectomy. In an atherectomy procedure, a guide catheter can be inserted into the patient's femoral artery and advanced until the distal end of the guide catheter is disposed near the patient's ostium or coronary artery. A guidewire can be inserted into the guide catheter and further advanced into the coronary artery, distally past the occluded region. A therapeutic atherectomy catheter having an atherectomy burr may be advanced over the guidewire, through the guide catheter, and to the narrowed region. The atherectomy burr can be rotated at high speed, causing the plaque to be removed in small particles as the plaque is abraded by the atherectomy burr.

Endarterectomy techniques have been utilized in open chest surgeries. In the endarterectomy technique, an artery may be slit longitudinally along its length by a surgeon, commonly after clamping opposite ends of the exposed vessel. The surgeon may strip the internal plaque away from the vessel walls, and remove the plaque from the vessel through the slit. A significant cleaning procedure typically follows the removal procedure to increase the chance of success. In a high percentage of cases, the vessel thus treated may remain potent for a long time period, rather than rapidly becoming restenosed.

What would be desirable are endarterectomy techniques and devices for performing endarterectomy intravascularly. In particular, what would be advantageous are techniques for performing intravascular endarterectomy using a distant entry site, such as a radial artery entry near the groin.

SUMMARY OF THE INVENTION

The present invention includes methods and devices for removing plaque and separating plaque from blood vessels using intravascular catheters. Suitable catheters include carbon dioxide delivery catheters having an elongate shaft and a lumen therethrough, and a distal delivery orifice in communication with the lumen, and disposed near a blunt distal leading edge or end. The blunt distal end can be provided as part of a bulbous distal head, and the catheter can include a pressure sensor in communication with the shaft proximal end. The blunt distal end can be advanced from a remote site to a plaque containing target site. The catheter can be advanced along the plaque-vessel wall interface, while expelling carbon dioxide from the catheter distal end. The carbon dioxide pressure can cause the plaque to separate from the vessel wall along a plane of relative weakness, with the separation occurring ahead of the catheter distal end in some methods. In some methods, the catheter is used in conjunction with a vessel occlusion device to build up pressure near the target site, and puff up or expand the vessel walls.

Another aspect of the invention includes endarterectomy paddles, or blunt ended paddles, which may be disposed at the distal ends of catheter shafts or disposed at the distal ends of expandable jaw devices. The paddles may be used to separate plaque from vessel walls. One paddle includes distal carbon dioxide delivery orifices. Another paddle includes at least one ultrasound imaging and/or vibrating chip disposed on one or more sides of the paddle. Another paddle is coupled to a proximal mechanical vibrating device, which transmits mechanical vibrations to the distally disposed paddle.

In another method according to the present invention, an intravascular endarterectomy device is provided having one or more blunt-edged plaque-separating or dissecting members for separating plaque from vessel walls. The device can be used to separate plaque from the walls of the left main coronary artery. One device has a pair of blunt-edged separating members disposed at the outside of scissors members capable of being radially outwardly extended by foreshortening the scissors arms. The scissors device can be advanced through a guide catheter, and to the left coronary ostium. The blunt plaque separating elements can be moved outwardly by retracting a pull wire or shaft coupled to the scissors. The outwardly placed blunt dissecting elements can be advanced distally along the left main coronary artery walls until the plaque is encountered, with the blunt dissecting elements separating the plaque from the vessel walls.

In another method according to the present invention, an anchoring guide catheter is provided, which can include a distal annular face having multiple orifices therethrough, a main lumen, and a vacuum lumen. The vacuum lumen can be coupled to the distal orifices to provide suction through the orifices. One anchoring device includes a double walled outer tube, with a vacuum lumen disposed between the two outer walls. Another anchoring device includes a separate vacuum lumen.

The anchoring guide catheter can be used to position intravascular devices near the left main coronary artery and to provide backup, anchoring support to the devices once positioned. The anchoring support can be used to provide support for advancing plaque-separating devices along the left main coronary artery wall to separate plaque from the artery wall. In use, the anchoring guide catheter may be advanced to the left coronary ostium, either independently or over a guide wire. A therapeutic device may be advanced through the anchoring guide catheter main lumen. The anchoring guide catheter vacuum may be turned on and vacuum supplied to the distal orifices, providing suction to anchor the anchoring guide catheter distal face to the ostium through the applied suction.

The anchoring guide catheter may be periodically removed to allow coronary blood flow in some methods, and supplied with perfusing oxygenated blood flow in other methods. An anchoring device according to the present invention may be used in conjunction with distal occlusion devices or more distally positioned emboli capturing devices. The anchoring device may be used to provide support for the plaque separation devices described in the present application. After plaque separation has been accomplished, the separated plaque may be retracted within the anchoring device, and removed in some methods.

An anchoring guide catheter may also be used to guide and support percutaneous endaterectomy devices for long time periods by retroperfusing the coronary arteries. A negative pressure may be supplied to the anchoring guide catheter, providing suction at the guide catheter distal end. Blood may be pulled from the coronary artery, for example, the left main coronary artery. The blood may be removed from the patient through the pump used to create the negative pressure. The blood may be pumped under pressure through a tube and reintroduced to the patient through the femoral vein. Oxygen or oxygenated blood may be provided through a tube introduced through an A-V femoral connection, with the tube introducing oxygen or oxygenated blood at the coronary sinus, into coronary veins having a slight negative pressure. The oxygenated blood may be pulled through the coronary veins, capillaries, and coronary arteries before being pulled again through the main lumen of the suction anchoring device and into the pump. Intravascular endarterectomy devices may be introduced through suitable manifolds near the guide catheter proximal end to allow for removing plaque from the left main coronary artery using the support provided by the anchoring guide catheter while retroperfusing the heart.

In another aspect of the invention, fine mesh stents are provided for use after endarterectomy. In one method, which may be suitable for use with percutaneous endarterectomy, the stent is self-expanding and can be delivered intravascularly through a delivery device. In another method, suitable for use after conventional endarterectomy, a stent is provided together with outwardly protruding, open staples. The stent may be inserted through the incision used to perform the endarterectomy, and the vessel walls on either side of the incision closed over the sharp staple ends, forcing the ends through the vessel walls, and the staples closed to both secure the stent and to close the incision.

DETAILED DESCRIPTION OF THE INVENTION

Figure 1A:
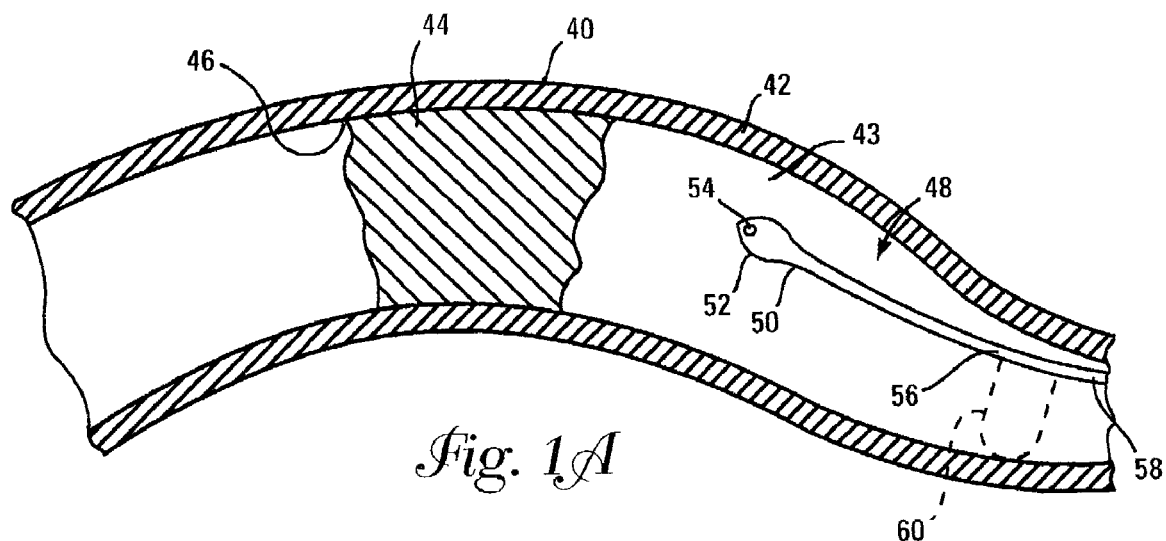
FIG. 1A is a fragmentary, highly diagrammatic, longitudinal, cross-sectional view of a vessel occluded by plaque being approached by a carbon dioxide infusing catheter having a bulbous distal end.

FIG. 1A illustrates a vessel 40 occluded by plaque 44 being approached by a carbon dioxide infusing catheter 48 having a bulbous distal head 52. Vessel 40 includes a vessel wall 42 and has plaque 44 attached to the vessel wall along an interface or separation plane 46. Catheter 48 has a distal region 50, a shaft 56, and a lumen 58 extending therethrough in fluid communication with a distal orifice 54. Catheter 48 can be formed of any suitable material, including metals and polymers. Some catheters are formed of Nitinol, while others are formed of stainless steel.

Catheter 48 may optionally be used with an occlusion device 60, shown in phantom in FIG. 1A. Occlusion device 60 may include an expandable or inflatable balloon or cuff. Occlusion device 60 may be configured to have a central orifice therethrough, disposed to allow passage of catheter 48 through the central orifice, followed by inflation, as illustrated by balloon 61 of FIG. 1D. In the embodiment illustrated in FIG. 1A, occlusion balloon 60 is configured to allow passage of catheter 48 around the side of the balloon, between the balloon and the vessel wall. Although not shown, it is considered that steerability may be added to the paddles to assist dissection by using guide catheters or by pull wires well known in the vascular art.

Figure 1B:
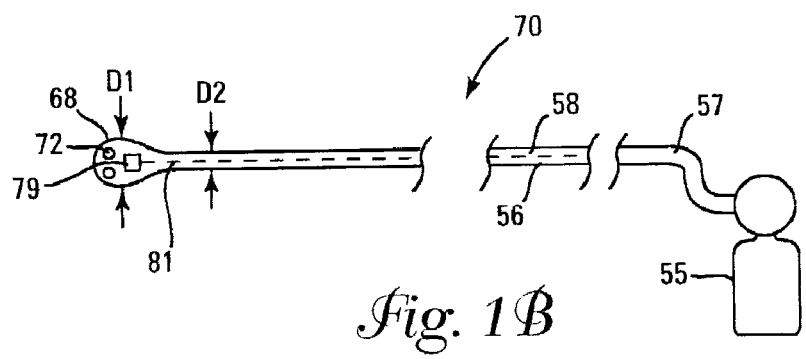
FIG. 1B is a fragmentary, highly diagrammatic, longitudinal, side view of a carbon dioxide infusing catheter having a bulbous distal head including two infusing ports and a pressure sensor, coupled to a carbon dioxide source.

FIG. 1B illustrates another carbon dioxide delivery catheter 70 having shaft 56 and lumen 58 as in catheter 48, further having a catheter proximal shaft region 57 coupled to a carbon dioxide source 55. Catheter 70 includes a bulbous distal head 68 having two distal orifices 72 therein for delivering carbon dioxide. In one embodiment, distal bulbous head 68 has a maximum width as indicated at D1, which is 50 percent greater than the width of the shaft width, as indicated at D2. Catheter 70 is sufficiently long to enable disposing distal bulbous head 68 in a coronary artery while controlling proximal shaft region 57 from an insertion site outside of the chest area. Catheter 70 is sufficiently long to enable insertion near the groin, followed by advancement to a coronary artery. Catheter 70 also includes a pressure sensor 79 coupled to a more proximal catheter region by data communication line 81. Pressure sensor 79 can be used to measure the pressure within the vessel, to provide an indication of the amount of carbon dioxide being supplied to the vessel.

Figure 1C:
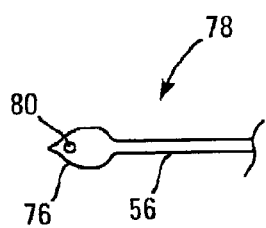
FIG. 1C is a fragmentary, highly diagrammatic, longitudinal, side view of a carbon dioxide infusing catheter having a spade shaped distal head including a single infusing port.

FIG. 1C illustrates another catheter 78, having a spade shaped distal head 76 and orifice 80, distal head 76 including more angular distal most features than catheter 70 of FIG. 1B. In one embodiment, the more angular features of catheter 78 are present in a side view, the distal head being cone-shaped. In another embodiment, distal head 76 has a flat, relatively constant thickness when viewed from the side. Carbon dioxide delivery catheters according to the present invention have a blunt, rather than sharp, distal leading edge.

Figure 1D:
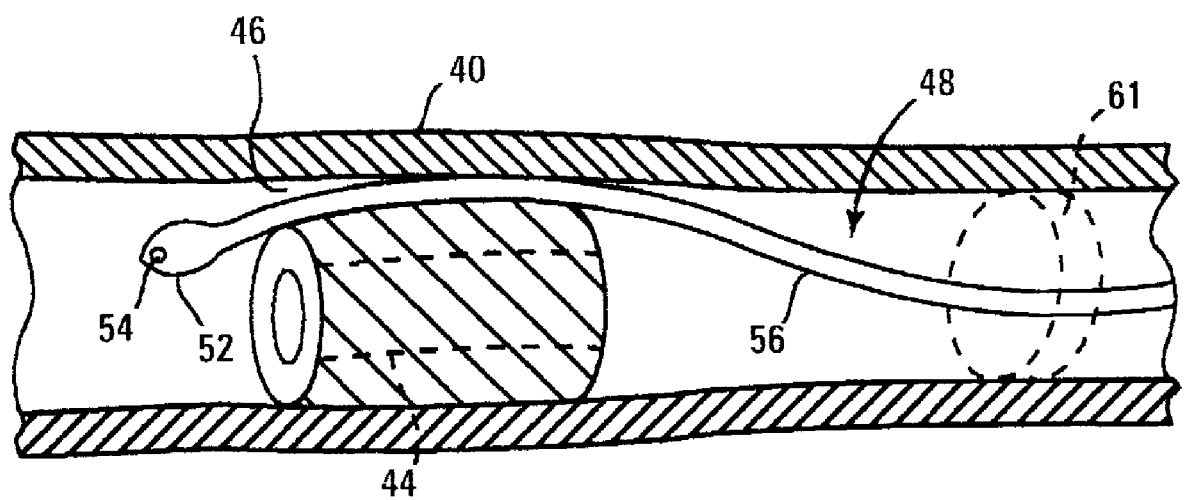
FIG. 1D is a fragmentary, highly diagrammatic, longitudinal, cross-sectional view of the vessel of FIG. 1A, having been crossed by the carbon dioxide infusing catheter along a plaque-vessel wall separation plane.

FIG. 1D illustrates vessel 40 and plaque 44 of FIG. 1A, having been crossed by carbon dioxide infusing catheter 48 along plaque-vessel wall separation plane 46. The plaque-vessel wall separation plane is a plane of natural weakness or relative weakness between the plaque and the vessel wall. By advancing catheter distal head 52 while carbon dioxide is being expelled from orifice 54, the naturally weakest areas are opened between plaque 44 and vessel wall 40. The carbon dioxide may find its way through the weakest planes, exploiting and adding to that weakness. The expelled carbon dioxide pressure may thus be used to ply the plaque atraumatically from the vessel wall. In some methods, carbon dioxide is supplied at a pressure sufficiently high to create a high velocity, low flow of 40-60 me/sec as small jets of carbon dioxide. The pressure can be adjusted to "puff" the vessel out to assist in separating the plaque from the vessel wall. In some methods, the pressure is regulated by providing an exhaust lumen through the catheter shaft, and controllably allowing carbon dioxide to escape, keeping an elevated physiologic pressure of 150 to 300 mm hg within the vessel. In some methods, the carbon dioxide pressure is maintained, with the assistance of an occlusion device, sufficiently high to give back flow in the artery. The carbon dioxide delivery catheter can be repeatedly retracted and advanced along different portions of the plaque.

Figure 2A:
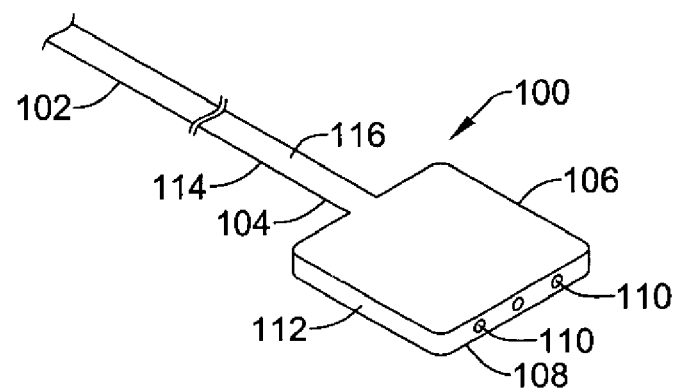
FIG. 2A is a fragmentary, highly diagrammatic perspective view of an endarterectomy paddle having distal carbon dioxide delivery orifices.

FIGS. 2A through 2E illustrate endarterectomy paddles which may be disposed at the distal ends of catheter shafts or disposed at the distal ends of expandable jaw devices, discussed further with respect to other drawings below. FIG. 2A illustrates an endarterectomy paddle device 100 having a shaft 114, a proximal region 102, a distal region 104, a blunt distal end 108, and a lumen 116 in fluid communication with distal carbon dioxide delivery orifices 110. Paddle 100 has a thickness indicated at 112 and a distal paddle 106 disposed on shaft distal region 104. Carbon dioxide can be delivered through device 100 and used to separate plaque, as described with respect to the carbon dioxide delivery devices previously discussed.

Figure 2B:
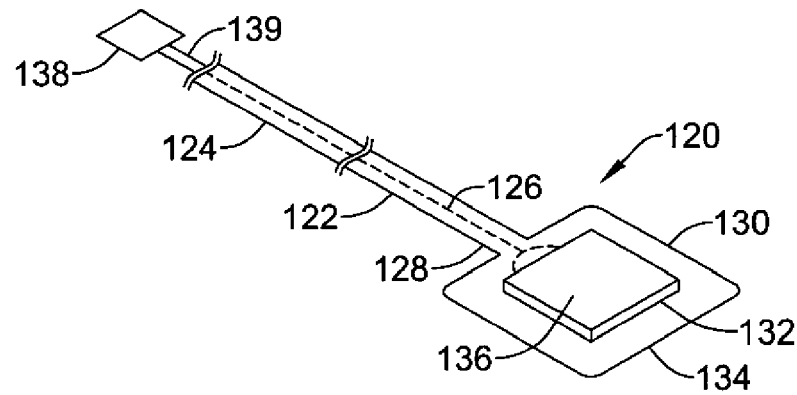
FIG. 2B is a fragmentary, highly diagrammatic, perspective view of an endarterectomy paddle having at least one ultrasound imaging chip.

FIG. 2B is an endarterectomy paddle device 120 having a shaft 122, a proximal region 124, a distal region 128, a distally disposed paddle 130, a blunt distal end 134, and an ultrasound imaging chip 132 having an outer surface 136. Ultrasound imaging chip 132 is coupled to an appropriate signal generator 138 through wires 139 and wires or electrodes 126. Ultrasound imaging chip 132 may include a transducer, well known to those skilled in the art, which can be used to transmit and receive ultrasound to image the surrounding vessel and any plaque. Blunt end 134 may be used to separate plaque from vessel walls, as previously described. Ultrasonic imaging chips may also be added to other paddles and distal edarterectomy devices, including the carbon dioxide delivery devices previously described.

Figure 2C:
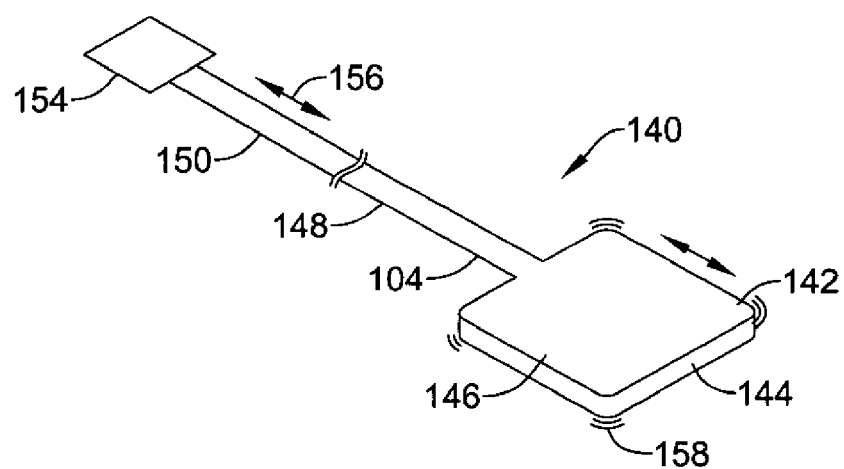
FIG. 2C is a fragmentary, highly diagrammatic perspective view of a mechanically vibrating endarterectomy paddle having a proximal mechanical vibrator.

FIG. 2C illustrates an endarterectomy paddle device 140 having a shaft 148, a proximal region 150, a distal region 152, and a distal paddle 142 having a blunt distal end 144. A proximally disposed mechanical vibrator 154 may be coupled to shaft proximal region 150 to vibrate paddle 142, as indicated at 156 and 158. Paddle 142 has a surface 146 which may contain an ultrasonic imaging chip, as previously described. Shaft 148 can be used to transmit the vibrations along the length of the shaft to paddle 142.

Figure 2D:
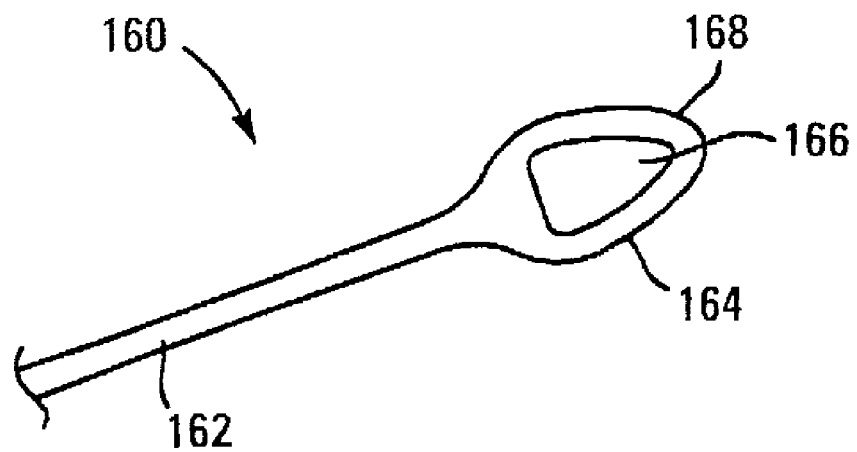
FIG. 2D is a fragmentary, highly diagrammatic, perspective view of an endarterectomy paddle having at least one ultrasound vibrating chip and having a blunt-ended, spade-shaped distal end.
Figure 2E:
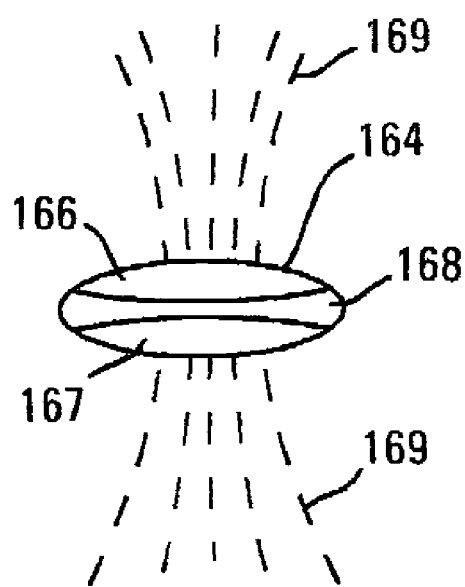
FIG. 2E is an end view of endarterectomy paddle of FIG. 2D, having two ultrasound vibrating chips.

FIG. 2D illustrates an endarterectomy paddle device 160 having a shaft 162 and a flat, spade-shaped distal paddle 164 having a blunt distal end 168 and a first ultrasonic vibrating chip 166. An electronic signal generator, not requiring illustration, may be coupled through electrodes in shaft 162 to chip 166. FIG. 2E illustrates an end view of endarterectomy paddle device 160, having first ultrasonic vibrating chip 166 and a second ultrasonic vibrating chip 167 disposed on the opposing side of paddle 164. Ultrasound signals being transmitted by chips 167 and 168 are indicated at 169, sufficient to vibrate the paddle.

Figure 3A:
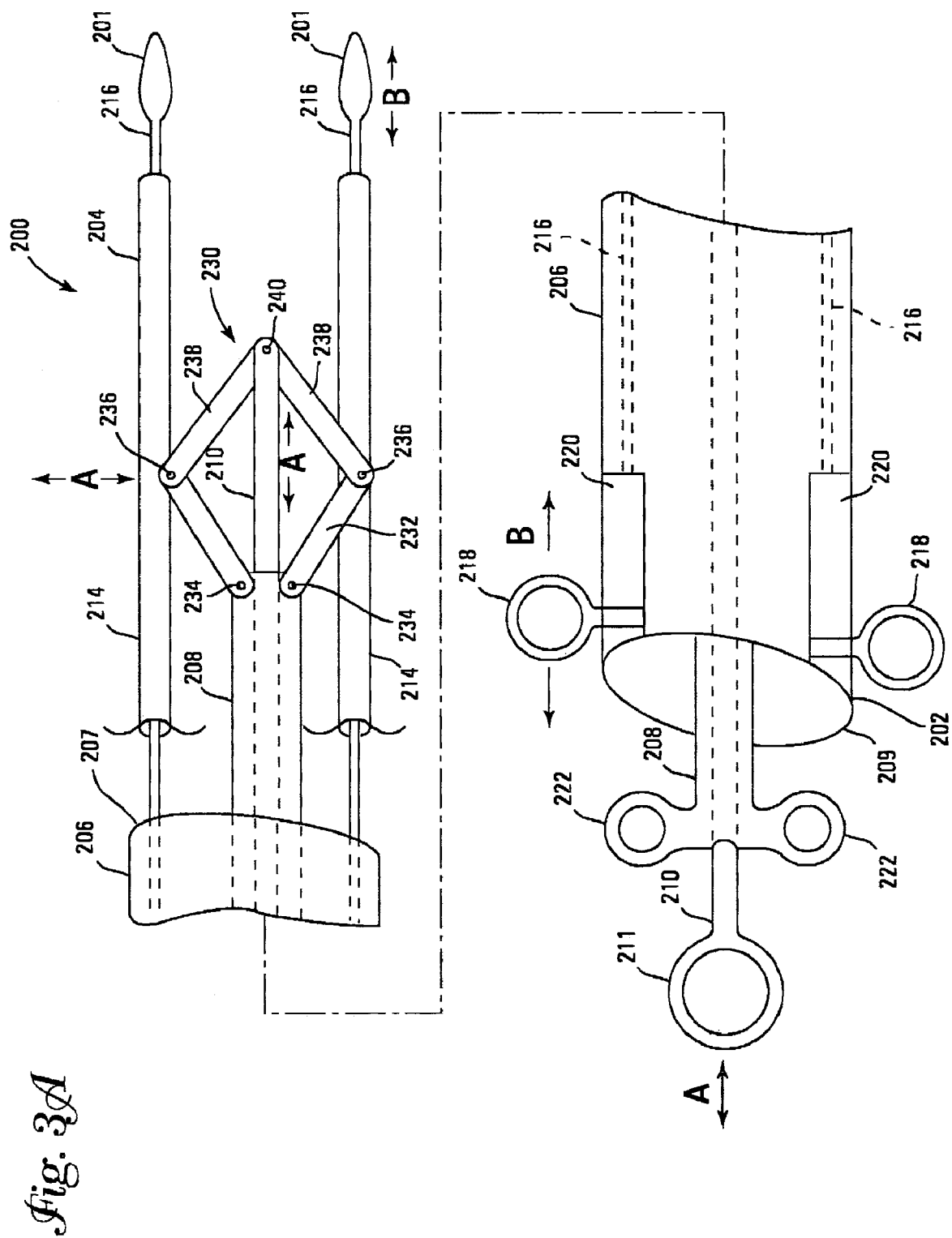
FIG. 3A is a fragmentary, highly diagrammatic, perspective partially cutaway view of an intravascular endarterectomy device having expandable distal endarterectomy paddles.

FIG. 3A illustrates an intravascular endarterectomy device 200 having a pair of expandable distal endarterectomy paddles 201. Lines "A" are used to denote movements associated with radially expanding the device, while lines "B" are used to denote movements associated with longitudinally extending the paddles. Device 200 has a proximal region 202 and a distal region 204. Device 200 includes an outer tube 206 slidably disposed about an intermediate or inner tube 208. Outer tube 206 has a proximal end 209. Intermediate tube 208 is disposed about an inner shaft 210, where inner shaft 210 is coupled to a ring 211 for slidably moving shaft 210 within inner tube 208. Inner tube 208 is coupled to rings 222 for slidably moving inner tube 208 within outer tube 206, and for maintaining the position of inner tube 208 with respect to outer tube 206 and inner shaft 210, when desired. Outer tube 206 has been illustrated as cutaway at 207, to better illustrate a pair of guiding tubes 214 disposed within, where guiding tubes 214 can be fixedly attached to outer tube 206, and where guiding tubes 214 need not extend proximally to outer tube proximal end 209. Within each guiding tube 214 is a slidably disposed paddle shaft 216 which can be distally coupled to distal paddle 201 and proximally coupled to rings 218. Rings 218 can be slidably disposed within slots 220. Axially moving rings 218 within slots 220 can move paddle shafts 216 and paddles 201.

Inner tube 208, with a pair of rings 222, may be fixedly disposed within outer tube 206 in some embodiments, and slidably disposed in others. An expandable scissors device 230 is disposed at the distal end of inner tube 208. Scissors device 230 includes first scissor arms 232 pivotally mounted at 234 to inner tube 208. Second scissor arms 238 may be pivotally mounted to both first scissor arms 232 and guiding tubes 214 at pivot points 236. Second scissor arms 238 may be pivotally mounted both to each other and to inner shaft 210 at pivot point 240.

In use, outer tube 206, together with inner tube 208 and inner shaft 210, may be advanced to near a target site. Paddles 201 may be proximally retracted, and inner shaft 210 distally extended, maintaining scissors 230 in a collapsed configuration. Once near the target site, inner shaft 210 may be retracted relative to inner tube 208, thereby expanding scissors 230 outward, along with guiding tubes 214 and paddles 201. Paddles 201 may be expanded against the vessel wall, proximal of the plaque-occluded site. Device 200 may be distally advanced as a whole, thereby distally advancing paddles 201 as well. Rings 218 may also be slid distally, causing paddles 201 to advance.

In devices having guiding tubes 214 secured in some manner to outer tube 206, paddle shafts 216 may angle outward somewhat upon the expansion of scissors 230. In some embodiments having guiding tubes less secured, paddle shafts 216 may maintain a more parallel orientation with respect to the vessel walls. Device 200 may be described generally as a device having a radially expandable distal portion which can longitudinally foreshorten and radially expand under the tension applied, for example, by a proximally retracting shaft secured to a location disposed distally of the portion to be longitudinally foreshortened. Paddles 201 may also be referred to as blunt dissection paddles, and device 200 may be referred to as a radially expandable blunt dissection device.

Figure 3B:
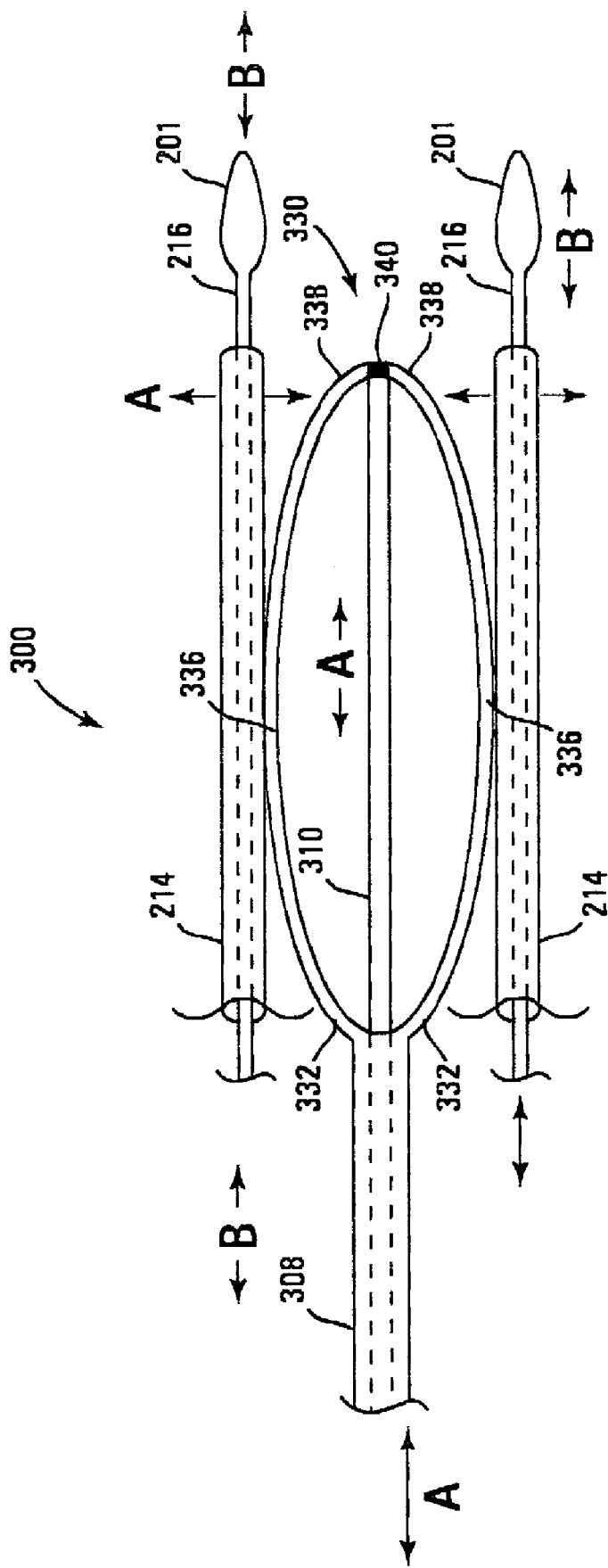
FIG. 3B is a fragmentary, highly diagrammatic, perspective partially cutaway view of the distal portion of an intravascular endarterectomy device having expandable distal endarterectomy paddles.

Paddles 201 may thus be moved outwardly and distally to separate plaque from enclosing vessel walls. Paddles 201 may be advanced along the vessel walls past the plaque. Paddles 201 may be retracted, rotated, and advanced in some methods to better separate the plaque from the vessel walls. In some methods, paddles 201 are used primarily to grasp plaque which has already been separated from the vessel walls by other methods. In some methods, after advancing paddles 201 distally past and over the plaque, paddles 201 may be pulled inward, or collapsed, which can better retain the captured plaque. The captured plaque may then be proximally retracted and removed from the vessel FIG. 3B illustrates the distal portion of another intravascular endarterectomy device 300, which can be similar in some respects to device 200 of FIG. 3A, sharing some commonly numbered and similar elements, but having a different scissors device 330. Lines "A" are used to denote movements associated with radially expanding the device, while lines "B" are used to denote movements associated with longitudinally extending the paddles. Scissors device 330 incorporates flexible arm members, rather than pivotally mounted members as in device 200 of FIG. 3A. Scissors device 330 includes flexible arm members including proximal arms 332 and distal arms 338 secured to guiding tubes 214 at attachment regions 336. Flexible arm members 332 and 338 may be formed of a single material piece in some devices. Distal arms 338 are secured to a central pull wire or shaft 310 at 340, and proximal arms 332 secured to an inner tube 308. Arms 332 and 338 may be biased to remain in an extended, radially closed position in some devices. In devices having a distally extended biased configuration, the central pulling member may be a pull wire 310, or optionally a shaft. In some embodiments, more than two flexible arms are provided. In one embodiment, four flexible arms are provided. In some embodiments, scissors device 330 is made by slitting the distal region of a tube, but leaving the distal most region unslit, thereby providing flexible arms able to foreshorten and splay radially outward when the distal most portion of the tube is retracted proximally. In operation and use, device 300 may be operated and used as described with respect to device 200 of FIG. 3A.

Figure 3C:
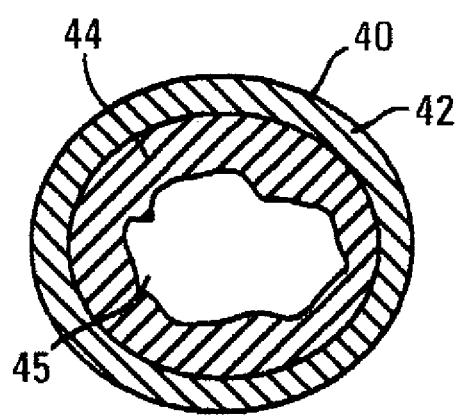
FIG. 3C is a highly diagrammatic, transverse, cross-sectional view of a partially occluded vessel prior to endarterectomy.
Figure 3D:
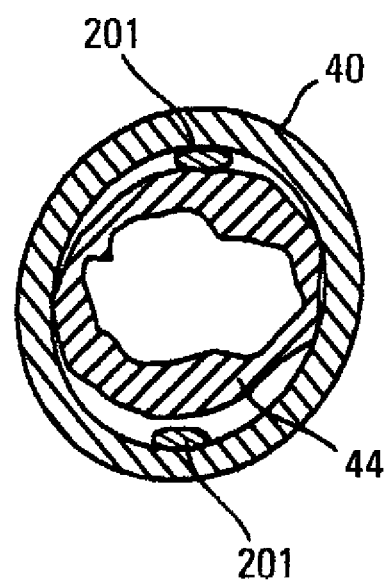
FIG. 3D is a highly diagrammatic, transverse, cross-sectional view of the partially occluded vessel of FIG. 3C, after endarterectomy paddles have been disposed between the plaque and the vessel walls.

FIG. 3C illustrates a transverse, cross-sectional view of vessel 40, having plaque 44 disposed within vessel walls 42 and having a lumen 45 through plaque 44. FIG. 3D illustrates plaque 44 after distal paddles 201 of device 200 have been radially expanded and distally extended around plaque 44, separating plaque 44 from vessel walls 42. It may be noted that paddles 201 have distended vessel walls 42 outward and away from plaque 44.

Figure 3E:
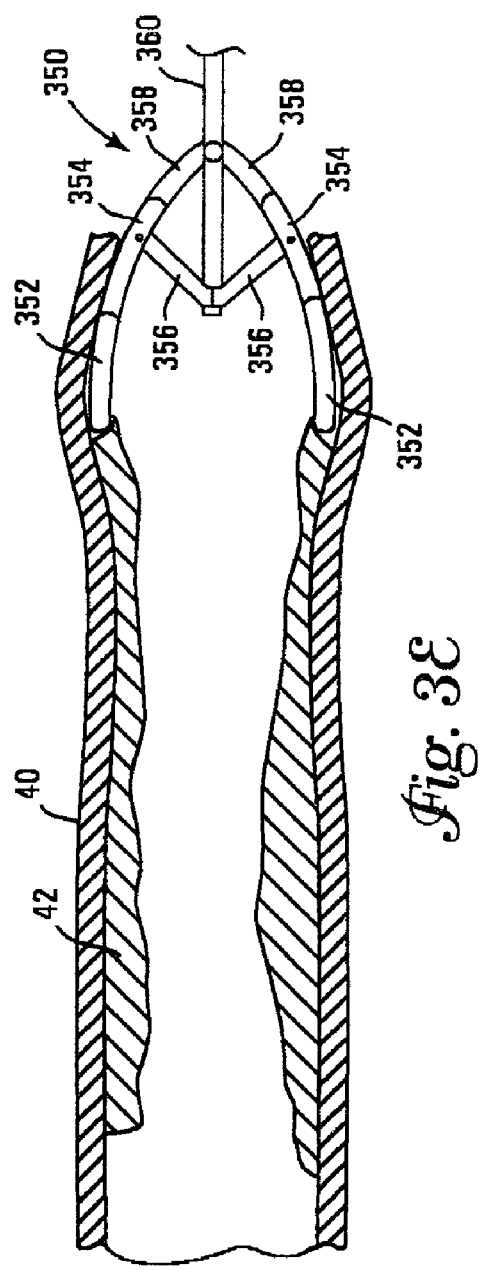
FIG. 3E is a highly diagrammatic, longitudinal, cross-sectional view of a partially occluded vessel after the longitudinally curved endarterectomy jaws of another device have been disposed between plaque and vessel walls.
Figure 3F:
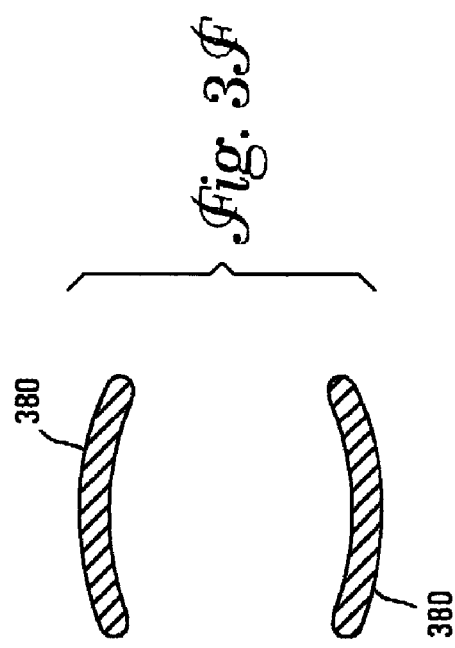
FIG. 3F is an end view of a pair of endarterectomy jaws that are circumferentially curved.

FIG. 3E illustrates another embodiment of a scissors device, with the distal portion of a device 350 being illustrated. A pair of longitudinally curved, opposed, jaws or dissection members 352 are illustrated having extension arms 354, and being attached along a pair of first scissors arms 358 which are joined to a pair of second scissors arms 356, which are coupled to a pull wire or shaft 360. Longitudinally curved jaws 352 may be better adapted to begin the separation of plaque from vessel walls in some devices. FIG. 3F illustrates an end view of one embodiment of jaws 380, similar to jaws 352 of FIG. 3E, that are curved circumferentially to better match the curvature of the vessel wall.

Figure 4A:
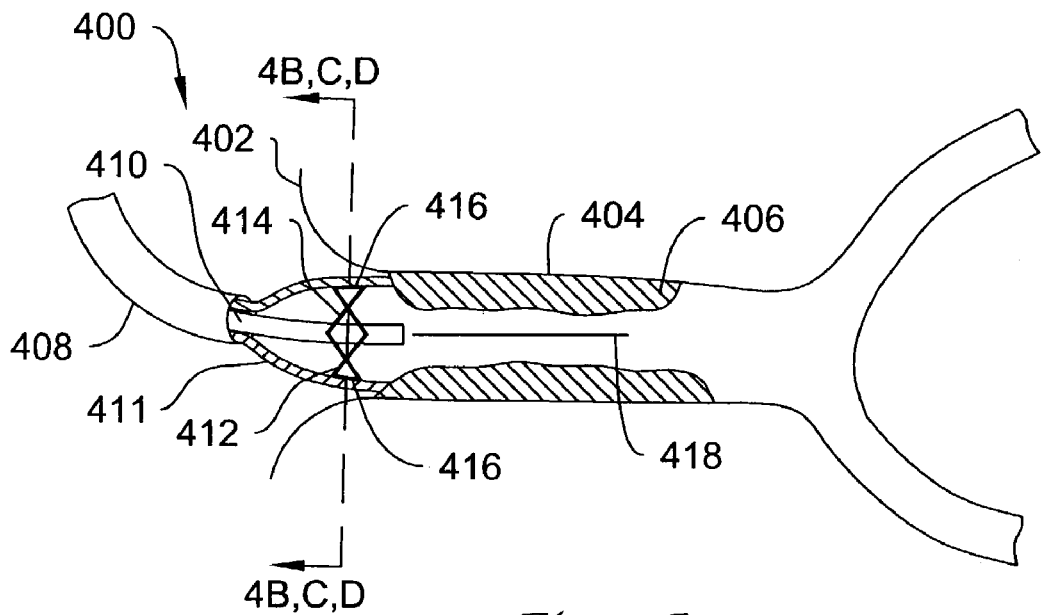
FIG. 4A is a highly diagrammatic, longitudinal, cross-sectional view through a partially occluded left main coronary artery having a guide wire, an intravascular endarterectomy device disposed over the guide wire, and a guide catheter disposed over the endarterectomy device.
Figure 4B:
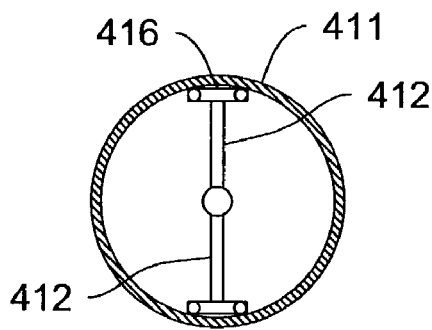
FIG. 4B is a cross section taken through FIG. 4A showing two jaw elements 416.
Figure 4C:
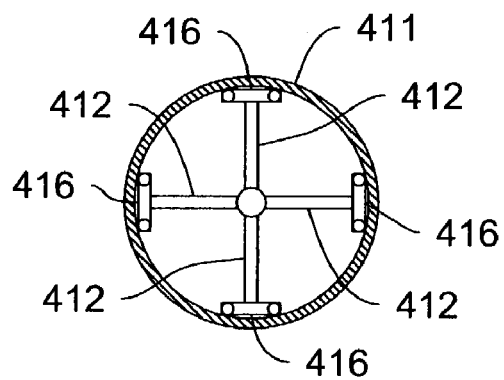
FIG. 4C is an alternative cross section having four jaw elements 416.
Figure 4D:
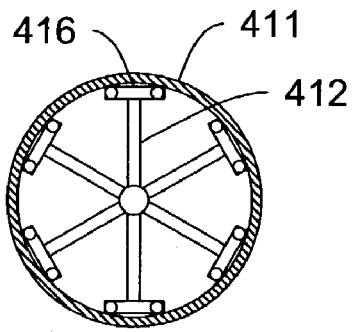
FIG. 4D is an alternative cross section having six jaw elements 416.

FIG. 4A illustrates another intravascular endarterectomy device 400 disposed within a guide catheter 408 and disposed over a guide wire 418. The left main coronary artery 404 is illustrated as partially occluded by plaque 406 near left coronary ostium 402. Blockages in the left main coronary artery may be difficult to treat. Device 400 is believed to be suitable to performing percutaneous endarterectomy on such a blockage. Device 400 includes a tube 410, an outer sheath 411, a first scissors arm 412 pivotally connected to a second scissors arm 414, and having a blunt jaw or separating element 416 disposed at the radially outermost extent of the first and second scissor arms. Jaw elements 416 may be radially expanded outward using retractable pull wires or shafts to longitudinally foreshorten the scissor arms and extend the jaws outward, as previously described with respect to other devices. FIGS. 4B, C and D are alternate cross sections taken from FIG. 4A showing device 410 having two, four and six jaw elements 416, respectively.

In one device, the distal portion of the scissors arm from each scissors pair is slidably disposed in a slot along the wall of tube 410, with the proximal portion of the other scissors arm pivotally disposed within a proximal portion of the slot. Proximally retracting the more distal arm portions can cause the scissors device to foreshorten and expand outward, presenting the blunt edges toward the artery wall. The expanded jaws may be advanced distally, thereby separating plaque 406 from left main artery wall 404. Providing a well-positioned and sufficiently well-anchored guide catheter 408 may greatly improve the use of devices removing plaque from the left main coronary artery.

Figure 5:
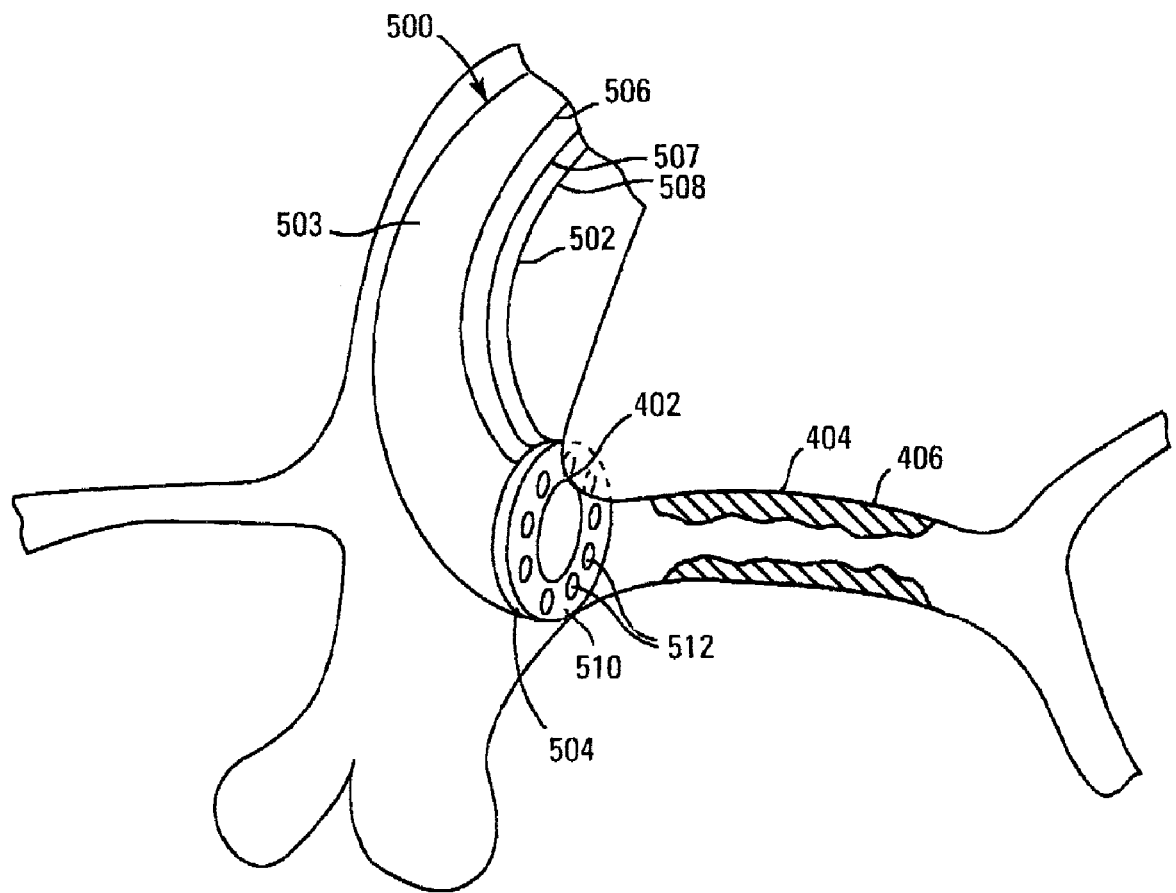
FIG. 5 is a highly diagrammatic, longitudinal, cross-sectional view through a partially occluded left main coronary artery having a suction ring guide catheter or anchoring device positioned over the left coronary artery ostium.

FIG. 5 illustrates a partially occluded left main coronary artery 404 having a suction ring guide catheter or anchoring device 500 positioned over the left coronary artery ostium 402. Anchoring device 500 has a distal region 508 including a distal end 504 having an annular ring 510 having a distal facing surface including multiple suction orifices 512. Anchoring device 500 also includes an outer tube wall 502, a lumen 503 therethrough, and an inner tube 506 having an inner tube wall 507. In one embodiment, outer tube wall 502 is a double wall having an annular lumen within which can function as a vacuum or suction lumen. The vacuum lumen can be in fluid communication with orifices 512, providing the suction needed to anchor distal face 510 to ostium 402. In another embodiment, inner tube 506 functions as a vacuum or suction tube, with inner tube 506 being coupled to orifices 512. In some embodiments, outer tube 502 and/or inner tube 506 are formed of Nitinol or stainless steel.

In use, anchoring device 500 can be advanced through the vasculature, in some methods, over a previously placed guide wire. The anchoring device may be advanced until distal annular ring 510 is disposed near ostium 402. In some methods, the therapeutic device to be guided through the anchoring device is advanced through anchoring device lumen 503. In one method, the therapeutic device can be an intravascular plaque separating device, for example, device 400 of FIG. 4. Such an intravascular device may be prepared by deploying the blunt plaque separating members outward.

Vacuum may be supplied through lumen 503, or other suction lumen, depending on the device. Anchoring device distal face 510 may be pressed against the region surrounding left coronary ostium 402. The vacuum, providing suction through distal orifices 512, may be used to anchor distal face 510 to the ostium region by forming a suction ring anostomosis. With anchoring device 500 firmly in place, intravascular devices may be advanced through the anchored device. In one method, the anchoring device is used to provide support for intravascular plaque removal device 400. With such support, additional distally directed force may be provided to drive plaque separating members between plaque and vessel walls.

Anchoring device 500, once in place, would temporarily block the supply of blood to the coronary arteries. In some methods, this is tolerated for a short period, followed by removal of the anchoring device. In some methods, lumen 503 is used to deliver an oxygen carrying substance to the coronary vessels for the duration of the procedure. In one method, oxygenated blood is supplied through lumen 503 to avoid angina during the procedure. In another method, an oxygenated blood substitute is provided through lumen 503. In some methods, an emboli capturing device, for example, an emboli filter, is deployed distally of plaque 406.

After an intravascular endarterectomy device has separated plaque 406 from the vessel wall, the plaque may be retrieved and retracted within lumen 503. In some methods, the same device used to separate the plaque is used to retrieve the plaque, while in other methods, a different device is used to retrieve the plaque. Examples of plaque separating devices that may be used in conjunction with anchoring device 500 may be seen in the plaque separating devices disclosed in the present application, as well as other devices.

Figure 6:
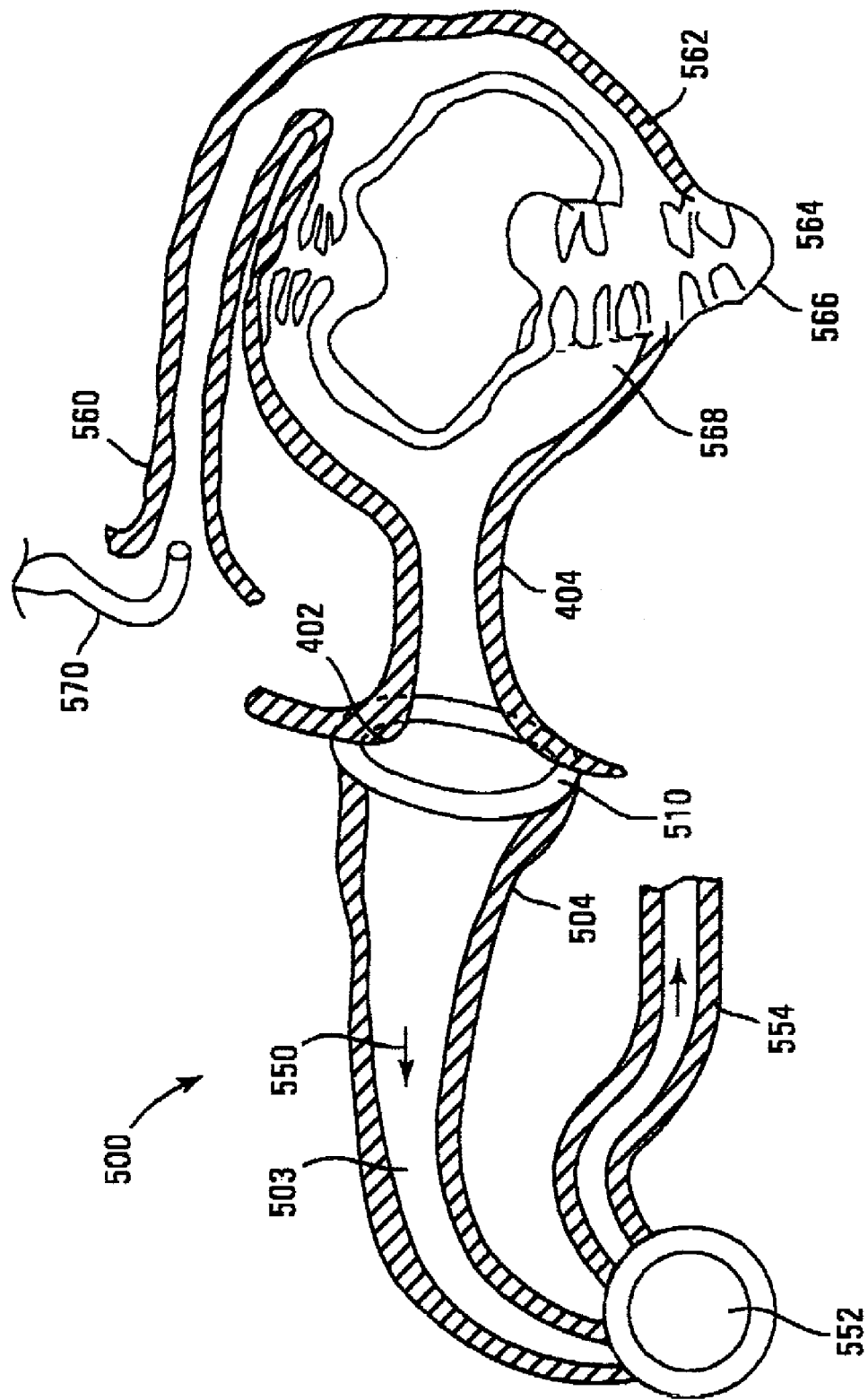
FIG. 6 is a schematic drawing of the anchoring guide catheter of FIG. 5, being used to retroperfuse the left coronary arteries.

FIG. 6 illustrates anchoring device 500 being used to retroperfuse a coronary artery. As previously discussed, forming the suction ring anostomosis between distal ring 510 and ostium 402 can cause interruption of blood supply to the coronary arteries. It has also been previously discussed that it is undesirable to allow pieces of plaque to be pulled downstream. A method is illustrated in FIG. 6 for allowing for the continued anchoring support of anchoring device 500, while supplying the coronary arteries with oxygen through the coronary veins and also removing any loose pieces of plaque.

A pump 552 may be coupled to anchoring guide catheter 500 to pull blood from left main coronary artery 404, as indicated at 550, through pump 552, out through a return tube 554, to be reintroduced to the patient through a site which can be the femoral vein. An oxygenated blood supply tube 570 is illustrated in a schematic fashion, for supplying oxygenated blood to the coronary veins. The oxygenated blood may be introduced through an A-V femoral connection to tube 570, which may be positioned near coronary sinus 560. The oxygenated blood may be pulled through coronary veins 562, through coronary capillaries 564 and 566, to coronary arteries 568, through left main coronary artery 404, and into anchor guide catheter main lumen 503.

Suitable manifolds may be disposed near the proximal end of anchoring guide catheter to allow for the introduction, manipulation, and control of intravascular endarterectomy devices within anchoring guide catheter 500. In some methods, a negative pressure of about minus 50 mm Hg is provided near the distal end of anchoring device 500, with a pressure of about 100 mm Hg resulting near the venous introduction of oxygenated blood to the coronary sinus. In some methods, the suction through the anchoring device main lumen is sufficient to anchor a guide catheter to the ostium, with a separate vacuum lumen and dedicated distal suction orifices not required. A guide catheter for left main coronary procedures may thus be provided that both removes possible emboli and perfuses the coronary muscles with oxygenated blood, all while providing support for left main endarterectomy procedures.

Figure 7:
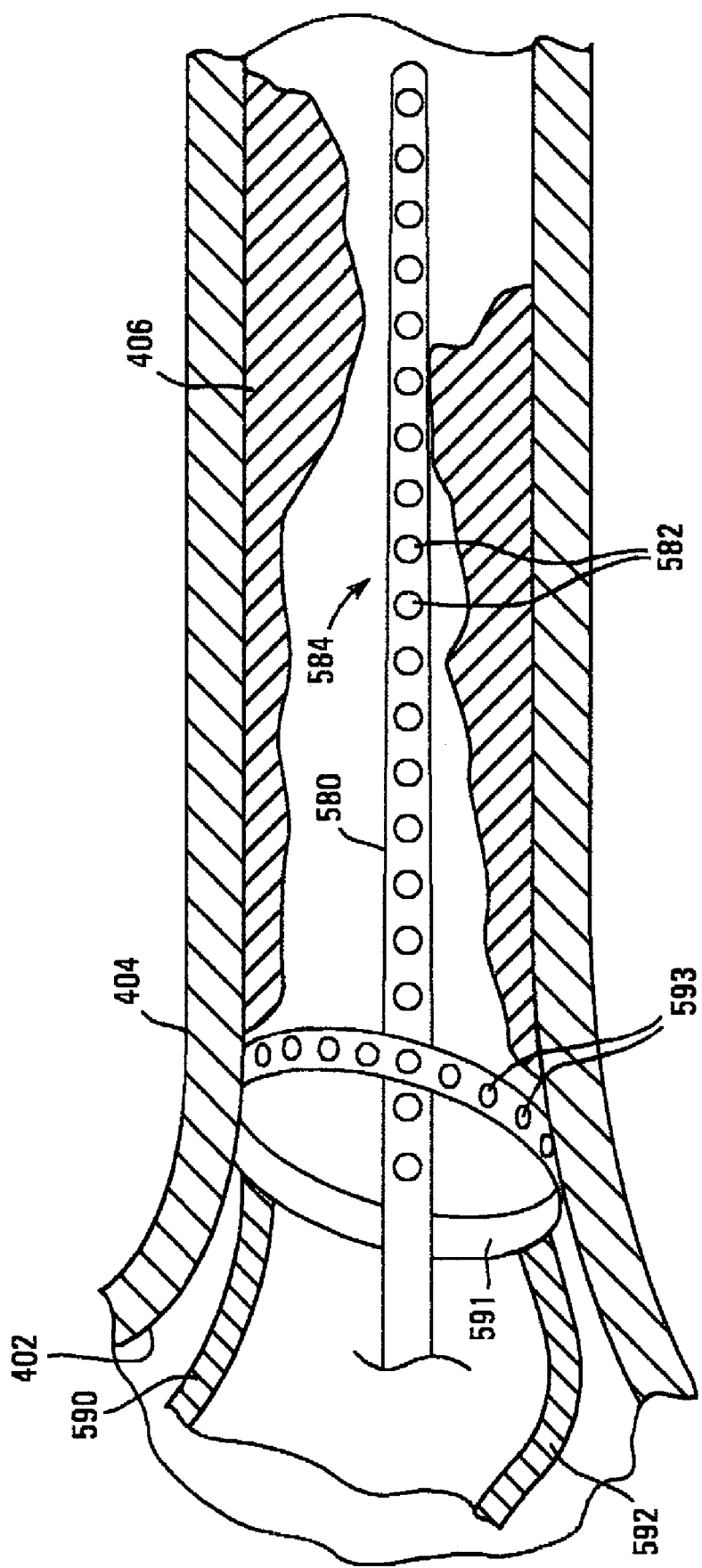
FIG. 7 is a highly diagrammatic, longitudinal, cross-sectional view of an anchoring guide catheter being used to guide an ultrasonic imaging probe into the left main coronary artery.

FIG. 7 illustrates an anchoring guide catheter 590, having a distal region 592, and a suction ring 591 with suction orifices 593 outwardly disposed, being used to guide an ultrasonic imaging probe 584 into left main coronary artery 404. Imaging probe 584 includes generally a shaft 580 and multiple ultrasonic imaging rings 582 disposed along the probe length. Imaging rings 582 extend around sides of shaft 580, providing a complete, or at least a partial, 360-degree image of the left main coronary artery. The information provided by the ultrasonic transducers can be used to create a map of the left main coronary artery, which can be used to formulate a plan for removing the plaque from the left main coronary artery.

Figure 8:
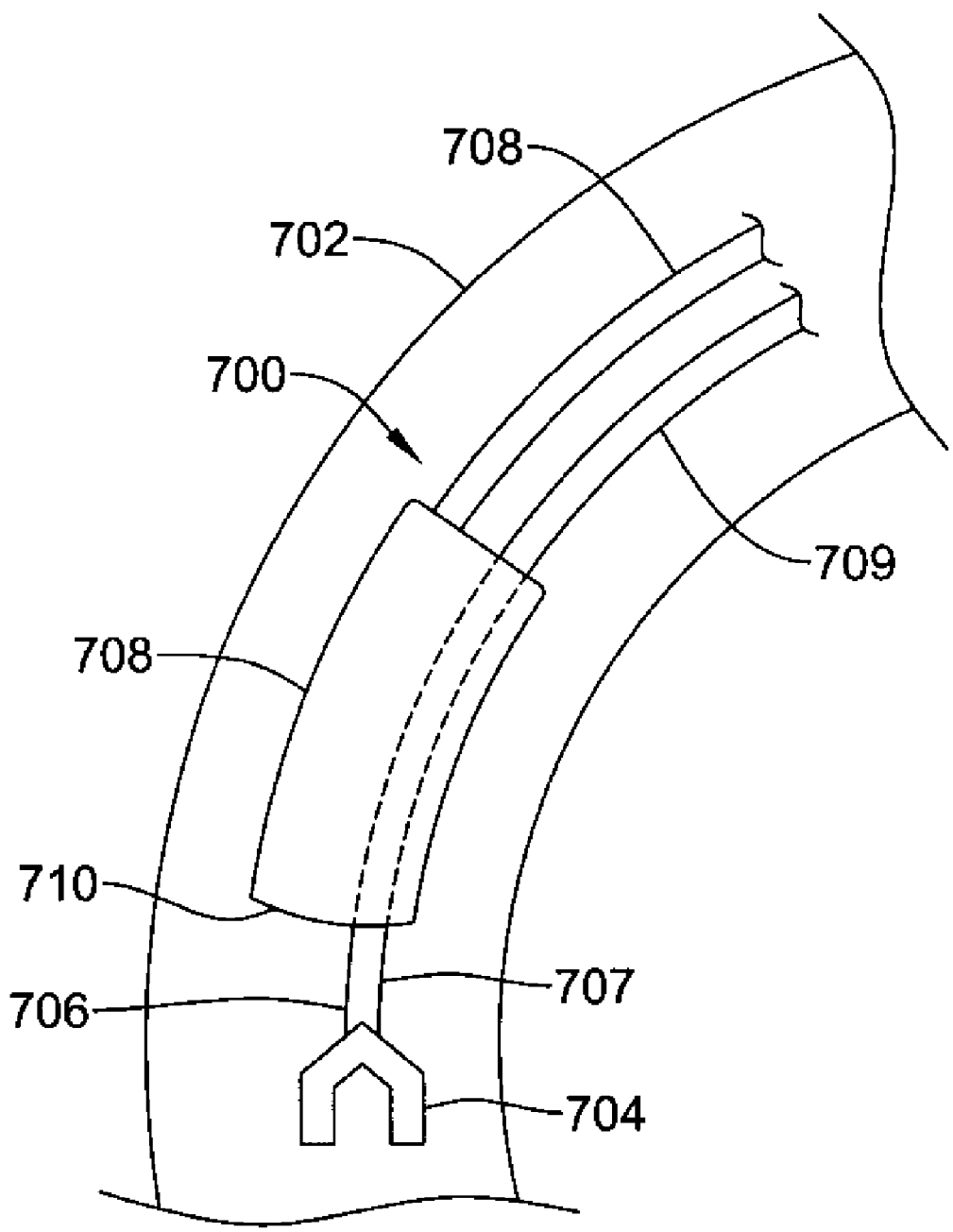
FIG. 8 is a highly diagrammatic, longitudinal, cross-sectional view through a plaque disposal chamber having a plaque removal device disposed through the device within the aorta.

FIG. 8 illustrates a plaque disposal device 700 having a plaque separating device 707 disposed through the device within the aorta 702. Plaque disposal device 700 includes a disposal chamber 708 having a lumen therethrough, and having a plaque separating device 707 disposed therethrough, including a shaft 706 and distal jaws or paddles 704. Plaque separating device 707 may be viewed generally as representing the plaque separation and removal devices described elsewhere in the present application. Chamber 708 is coupled to a shaft or tube 709 which may include a suction lumen in some embodiments, and control lines in other embodiments. Chamber 708 may be an enclosure to capture plaque that has been pulled into the chamber, for example, through a tight, distal elastic orifice 710. In some embodiments, chamber 708 includes mechanical devices and/or chemical compounds to grind and/or dissolve or destroy plaque that is brought into the chamber. Some embodiments perform grinding through rotablating, while others ablate the plaque through ultrasound. Some embodiments grind the plaque in grit to further reduce the plaque particles. The reduced size plaque particles may then be removed through suction, through tube 708.

Figure 9A:
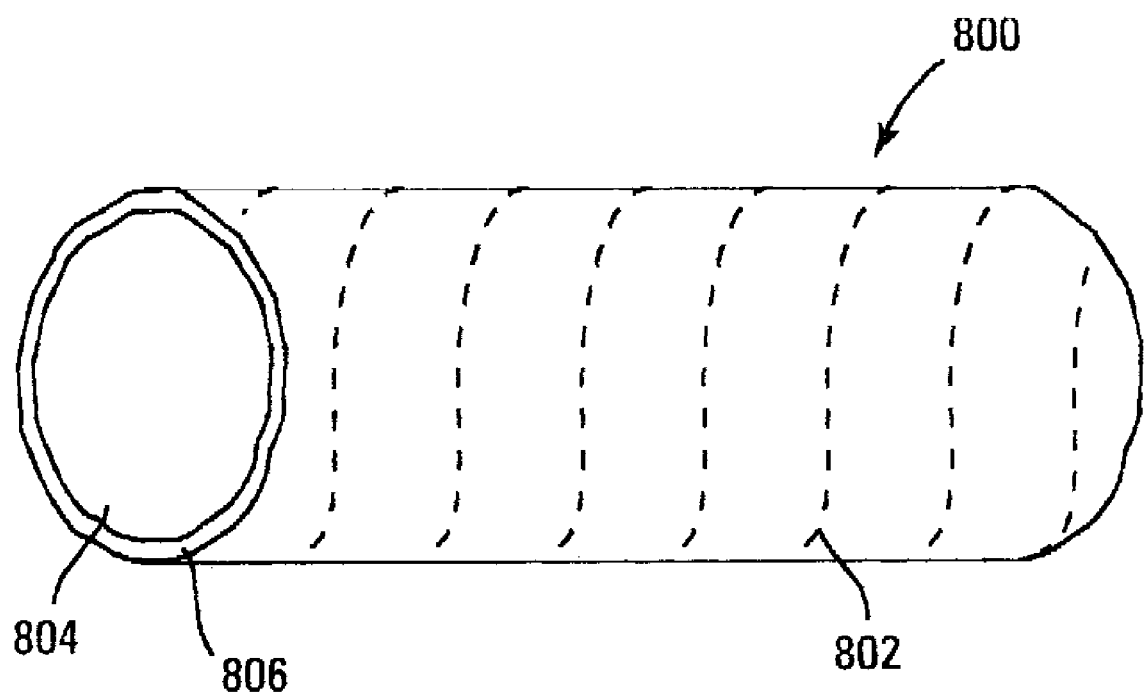
FIGS. 9A-9C are highly diagrammatic, perspective views of liners that may be used to line vessels after plaque has been removed through endarterectomy.

FIG. 9A illustrates a stent or liner 800 that may be used to line vessels after plaque has been removed through percutaneous endarterectomy. Liner 800 includes a sleeve or wall portion 802, an end 806, and a lumen 804 therethrough. Endarterectomy may leave a rough or shaggy vessel inner surface that may cause less than optimal healing after the procedure removes the plaque. Stent 800 has sufficient hoop strength to self expand after being released from a delivery device. The hoop strength should be strong enough to expand against the artery wall, but need not be strong enough to provide vessel structural support. Sleeve 802 may be formed of a single material, or may be formed of an inner material and an outer lining material. Suitable lining materials may include fine metal wires, PTFE, Dacron, and urethane. Materials such as Nitinol may also be included within sleeve 802, and may be in woven, braided, or coiled form. Sleeve 802 is formed of a very fine woven or mesh material.

Figure 9B:
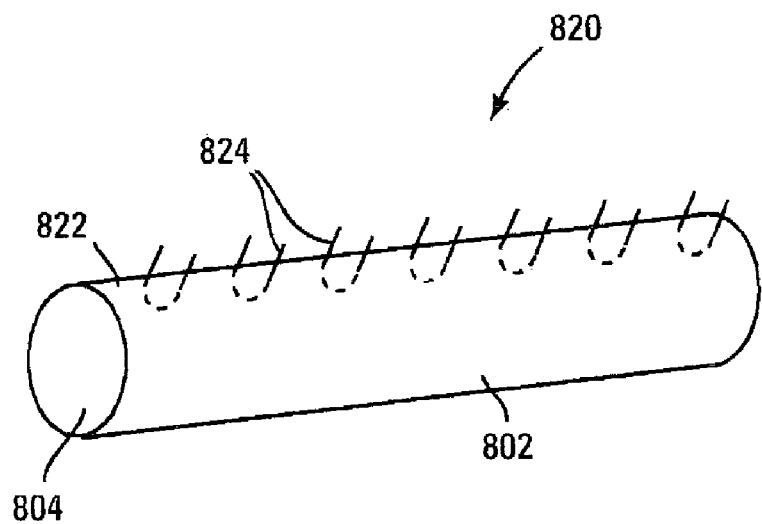
Figure 9C:
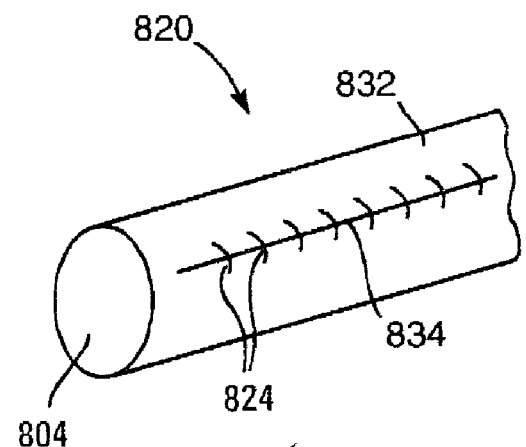

FIGS. 9B and 9C illustrate a stent or liner 820 that may be used to line vessels after plaque has been removed through conventional endarterectomy. Liner 820 includes wall or sleeve portion 802 and lumen 804 as previously described. Liner 820 also includes a longitudinal strip 822 having several staples 824, in open position, protruding therefrom. In use, after a conventional endarterectomy procedure, an incision 834 typically remains in the vessel wall 832, requiring closure. Stent 820 may be inserted through the incision, and vessel wall 832 forced over the open staples, forcing the staple ends through vessel wall 832 on either side of incision 834. The staples may be closed over incision 834, providing an alternative to stitches for closing the incision, and, in addition, providing a stent for improved postoperative results.

Numerous advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The invention's scope is, of course, defined in the language in which the appended claims are expressed.

What is claimed is:

1. A percutaneous method for separating plaque from a target site vessel interior wall, the method comprising the steps of:
    providing an elongate tubular member having a distal end, a proximal region, a lumen therethrough, and at least one distal orifice in fluid communication with the lumen and disposed in the tubular member distal end;
    providing a carbon dioxide source in fluid communication with the elongate tubular member lumen in the proximal region;
    inserting the tubular member distal end into the vasculature at a remote entry site;
    advancing the tubular member distal end through the vasculature to near the target site;
    infusing the carbon dioxide into the lumen and through the distal orifice; and
    separating the plaque from the vessel wall by further advancing the tubular member distal end along the target site vessel wall while expelling carbon dioxide from the tubular member distal end.

2. A percutaneous method as recited in claim 1, wherein the inserting tubular member step includes inserting at the remote entry site at least 100 centimeters from the target site.

3. A percutaneous method as recited in claim 2, wherein the distal end is blunt, such that the separating step is achieved using the blunt end.

4. A percutaneous method as recited in claim 3, wherein the separating step is achieved by separating the plaque from the vessel wall along a region of weakness by infusing the carbon dioxide.

5. A percutaneous method as recited in claim 4, wherein the tubular member distal end has a bulbous shape.

6. A percutaneous method as in claim 5, wherein the tubular member bulbous distal end has an outer diameter at least 50 percent greater than the outer diameter of a tubular member distal region disposed just proximal of the bulbous distal end.

7. A percutaneous method as in claim 2, wherein the tubular member includes a distal pressure transducer for measuring vessel fluid pressure near the distal end, and the method includes adjusting carbon dioxide inflow in response to a signal from the distal pressure transducer.

8. A percutaneous method as in claim 2, wherein the target site is within a coronary artery, and the remote entry site is located further away than the chest area.

9. A percutaneous method for separating plaque from a target site vessel wall, the method interior wall, the method comprising the steps of:
    providing an elongate tubular member having a distal region and a proximal region, wherein the distal region has a distal paddle having a width and a thickness, wherein the width is larger than the thickness, wherein the paddle has a blunt distal edge;
    inserting the tubular member distal paddle into the vasculature at a remote entry site;
    advancing the tubular member distal paddle through the vasculature to near the target site; and
    separating the plaque from the vessel wall by further advancing the tubular member distal paddle blunt distal edge along the target site vessel wall.

10. A percutaneous method as recited in claim 9, wherein inserting paddle step includes inserting the paddle at the remote entry site at least 100 centimeters from the target site.

* * * * *